United States Patent [19]

Kinishi et al.

[11] Patent Number: 4,950,810
[45] Date of Patent: Aug. 21, 1990

[54] SELECTIVE PROCESS FOR PREPARTING 2,4- OR 3,6-DI-SUBSTITUTED PHENOL COMPOUNDS

[75] Inventors: Ryoichi Kinishi; Shuichi Wakamatsu, both of Fukuoka; Tetsuji Ike, Nakatsu, all of Japan

[73] Assignee: Yoshitomi Pharmaceutical Industries, Ltd., Osaka, Japan

[21] Appl. No.: 330,062

[22] Filed: Mar. 29, 1989

[30] Foreign Application Priority Data

Mar. 30, 1988 [JP] Japan .................. 63-79548
Mar. 30, 1988 [JP] Japan .................. 63-79549

[51] Int. Cl.$^5$ .............................. C07C 37/14
[52] U.S. Cl. ......................... 568/790; 568/785
[58] Field of Search ............. 568/790, 794, 785

[56] References Cited

U.S. PATENT DOCUMENTS

| Re. 23,183 | 12/1949 | Arvin et al. | 568/790 |
|---|---|---|---|
| 2,371,550 | 3/1945 | Schaad | 568/790 |
| 2,415,069 | 2/1947 | Arvin et al. | 568/790 |
| 2,428,745 | 10/1947 | Stillson | 568/790 |
| 2,578,206 | 12/1951 | Pines et al. | 568/780 |
| 2,655,547 | 10/1953 | Bryner | 568/790 |
| 2,662,869 | 12/1953 | Bloch | 568/790 |
| 3,201,486 | 8/1965 | Bielawski et al. | 568/790 |
| 3,290,389 | 12/1966 | Hahn | 568/794 |
| 3,290,392 | 12/1966 | Ecke | 568/794 |
| 4,092,367 | 5/1978 | Bridwelle et al. | 568/790 |

FOREIGN PATENT DOCUMENTS

| 577710 | 6/1959 | Canada | 568/790 |
|---|---|---|---|
| 1111751 | 5/1968 | United Kingdom | 568/790 |

OTHER PUBLICATIONS

Desai, "Journal of the Colour Society", pp. 3–10, Jan–-Mar., (1978).
World Patent Index (Derwent) No. 74-29620V/16.
World Patent Index (Derwent) No. 86-033322/05.
World Patent Index (Derwent) No. 86-275561/42.

Primary Examiner—Werren B. Lone
Attorney, Agent, or Firm—Wenderoth, Lind & Ponack

[57] ABSTRACT

A selective process for preparing a 2,4- or 3,6-di-substituted phenol compound which comprises reacting an olefin compound of the formula:

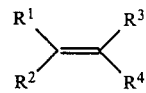

wherein $R^1$ is hydrogen, halogen, alkyl, halogen substituted alkyl, aryl, halogen substituted-aryl or alkyl substituted-aryl; and $R^2$, $R^3$ and $R^4$ are the same or different and each is hydrogen, halogen, alkyl, halogen substituted-alkyl or aralkyl; with a phenol compound of the formula:

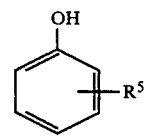

wherein $R^5$ is hydrogen, hydroxy, halogen, alkyl, halogen substituted-alkyl, alkoxy or $-C(R^6)(R^7)CH(R^8)(R^9)$ (wherein $R^6$ is hydrogen, halogen, alkyl, halogen substituted-alkyl, aryl, halogen substituted-aryl or alkyl substituted-aryl; and $R^7$, $R^8$ and $R^9$ are the same or different and each is hydrogen, halogen, alkyl, halogen substituted-alkyl or aralkyl), in the presence of a phosphorus compound and a carboxylic acid compound as catalysts.

The methods of the present invention, which is used a phosphorus compound and a carboxylic acid compound as catalysts, are enable to make the separation procedures easy, make the reaction process and time short, not to produce any colored resultant product, and reduce that cost in manufacturing procedures.

7 Claims, No Drawings

SELECTIVE PROCESS FOR PREPARTING 2,4- OR 3,6-DI-SUBSTITUTED PHENOL COMPOUNDS

BACKGROUND OF THE INVENTION

The present invention relates to a novel process for preparing selectively 2,4- or 3,6-di-alkyl and di-aralkyl-phenol compounds which are very important as starting materials for loading materials of rubber, antioxidants, plasticizers, phenol resins or developers of the thermo-sensitive and pressure-sensitive recording sheets and so on.

As the methods for preparing the di-substituted phenol compounds, a method of alkylation and aralkylation on the phenol nucleus, or a method of transferation and a method of disproportionation generally are known.

In the alkylation and aralkylation on the phenol nucleus, it is known that hydrochloric acid, oxalic acid, phosphoric acid, p-toluenesulfonic acid, sulfuric acid, trifluoromethanesulfonic acid or alumina can be used as a catalyst according to Journal of the Colour Society, Vol. 17(1), p. 3-10, 1978, Spanish Pat. No. 336,838, Japanese Patent publication (Kokai) No. 48-86834, U.S. Pat. No. 3,290,389, French Pat. No. 1,484,640 and U.S. Pat. No. 3,290,392.

The product obtained by the above-mentioned references is only mono-substituted phenol or a mixture of mono-, di- or tri-substituted phenol and position isomers thereof. Namely, the di-substituted phenol compounds cannot be selectively produced by the catalysts used hitherto.

Further, it is well known that the amount of an olefin to a phenol compound have an effect on the composition of the resultant product. Using less than the theoretical amount of an olefin, however, the amount of the formed di-substituted phenol compounds are reduced, whereas by using more than the theoretical amount of an olefin, the poly-substituted phenol compounds are formed in large quantities and accordingly, the objective di-substituted phenol compounds are difficult to separate.

The methods of the transferation or disproportionation are described, for example, in Japanese Patent publication (Kokai) Nos. 60-255742 and 61-200934. According to such methods, at first poly-substituted phenol compounds are produced and then the obtained poly-substituted phenol compounds are converted to the di-substituted phenol compounds. As a result, the objective di-substituted phenol compounds are prepared by two steps, and cannot be satisfactorily obtained.

Such reaction product consists of a mixture of the various substituted phenol compounds and is considerably colored. Further, it is necessary to carry out more troublesome separation for the purification of the objective di-substituted phenol compounds. Consequently, the methods of the transferation or disproportionation have various disadvantages from the industrial viewpoint.

Therefore, in prerparing industrially useful di-substituted phenol compounds by means of the alkylation or aralkylation methods on the phenol nucleus, it has been desired to use catalyst which allows the reaction to perform selectively and by one step without causing the reaction of transferation or disproportionation.

SUMMARY OF THE INVENTION

The present invention provides a novel process which prepares selectively 2,4- or 3,6-di-alkyl and di-aralkylphenol compounds having an industrial utility, consists of one step and does not produce any colored resultant product.

DETAILED DESCRIPTION OF THE INVENTION

Namely, the present invention relates to a selective process for preparing a 2,4- or 3,6-di-substituted phenol compound (hereinafter, the phenols may be referred to as the compound (I)), which comprises reacting an olefin compound of the formula (II):

(II)

wherein $R^1$ is hydrogen, halogen, alkyl, halogen substituted-alkyl, aryl, halogen substituted-aryl or alkyl substituted-aryl; and $R^2$, $R^3$ and $R^4$ are the same or different and each is hydrogen, halogen, alkyl, halogen substituted-alkyl or aralkyl, with a phenol compound of the formula (III):

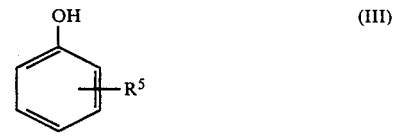
(III)

wherein $R^5$ is hydrogen, hydroxy, halogen, alkyl, halogen substituted-alkyl, alkoxy or $-C(R^6)(R^7)CH(R^8)(R^9)$ (wherein $R^6$ is hydrogen, halogen, alkyl, halogen substituted-alkyl, aryl, halogen substituted-aryl or alkyl substituted-aryl; and $R^7$, $R^8$ and $R^9$ are the same or different and each is hydrogen, halogen, alkyl, halogen substituted-alkyl or aralkyl); in the presence of a phosphorus compound and a carboxylic acid compound as catalysts.

In the definitions of each symbol of the above formulae, halogen means chlorine, bromine, fluorine and iodine; alkyl means straight or branched chain alkyl group having 1 to 8 carbon atoms such as methyl, ethyl, propyl, isopropyl, butyl, isobutyl, sec-butyl, tert-butyl, pentyl, isopentyl, hexyl, octyl, 2-ethylhexyl or 1,1,3,3-tetramethylbutyl; alkoxy means straight or branched chain alkoxy group having 1 to 8 carbon atoms such as methoxy, ethoxy, propoxy, isopropoxy, butoxy, isobutoxy, sec-butoxy and tert-butoxy; halogen substituted alkyl means straight or branched chain halogenated alkyl group having 1 to 4 carbon atoms such as fluoromethyl, chloromethyl, bromomethyl, iodomethyl, difluoromethyl, dichloromethyl, dibromomethyl, trifluoromethyl, fluoroethyl, chloroethyl, bromoethyl, iodoethyl, difluoroethyl, trifluoroethyl, fluoropropyl, chloropropyl, bromopropyl, iodopropyl, difluoropropyl, trifluoropropyl, fluorobutyl, chlorobutyl, bromobutyl, iodobutyl, difluorobutyl or trifluorobutyl; aryl means phenyl and naphthyl; halogen substituted-aryl means chlorophenyl, bromophenyl, fluorophenyl, iodophenyl, chloronaphthyl, bromonaphthyl, fluoronaphthyl or iodonaphthyl; alkyl substituted-aryl means aryl substituted by 1 to 3 straight or branched chain alkyl groups having 1 to 4 carbon atoms such as methylphenyl, ethylphenyl, propylphenyl, isopropylphenyl, butylphenyl, isobutylphenyl, sec-butylphenyl, tert-butylphenyl, dimethylphenyl or trimethylphenyl; aralkyl means phenylalkyl, wherein the alkyl moiety bears 1 to 4 carbon atoms, such as benzyl, 1-phenylethyl, 2-phenylethyl, 3-phenylpropyl or 4-phenylbutyl.

The objective compounds of formula (I) consist of 2,4-di-substituted phenol compounds of the formula (I-a):

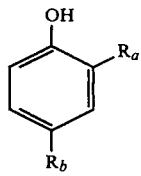

and 3,6-di-substituted phenol compounds of the formula (I-b):

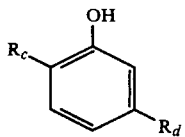

wherein $R_a$, $R_b$ and $R_c$ are the same or different and each is hydroxy, halogen, alkyl, halogen substituted-alkyl, alkoxy or —$C(R^6)(R^7)CH(R^8)(R^9)$ (wherein $R^6$ is hydrogen, halogen, alkyl, halogen substituted-alkyl, aryl, halogen substituted-aryl or alkyl substituted-aryl; and $R^7$, $R^8$ and $R^9$ are the same or different and each is hydrogen, halogen, alkyl, halogen substituted-alkyl or aralkyl); $R_d$ is hydroxy, halogen, alkyl, halogen substituted-alkyl, alkoxy or —$C(R^6)(R^7)CH(R^8)(R^9)$ (wherein $R^6$ is hydrogen, halogen, alkyl, halogen substituted-alkyl, aryl, halogen substituted-aryl or alkyl substituted-aryl; and $R^7$, $R^8$ and $R^9$ are the same or different and each is hydrogen, halogen, alkyl, halogen substituted-alkyl or aralkyl).

The objective compounds of formula (I-a) include, for example, 2,4-di-tert-butylphenol, 2-tert-butyl-4-methylphenol, 4-tert-butyl-2-methylphenol, 2-tert-butyl-4-ethylphenol, 4-tert-butyl-2-ethylphenol, 2-tert-butyl-4-(α-methylbenzyl)phenol, 2,4-di-(α-methylbenzyl)phenol, 2,4-di-(α,4-dimethylbenzyl)phenol, 2,4-di-(α,α-dimethylbenzyl)phenol, 2-(α-methylbenzyl)-4-methylphenol, 4-(α-methylbenzyl)-2-methylphenol and 2-(α-methylbenzyl)-4-ethylphenol, and the objective compounds of formula (I-b) include, for example, 6-tert-butyl-3-methylphenol, 6-tert-butyl-3-ethylphenol and 6-(α-methylbenzyl)-3-methylphenol.

According to the new methods of the present invention, the 2,4-di-substituted phenol compound of formula (I-a) can be prepared by reacting the olefin compound of formula (II) with one of the phenol compounds of the formula (III-a), (III-b) and (III-c):

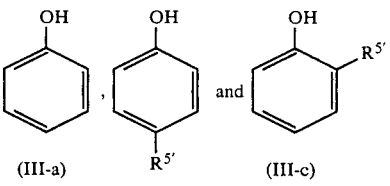

wherein $R^{5'}$ is the same as $R^5$ other than hydrogen.

The olefin compound of formula (II) includes, for example, ethylene, propylene, 1-butene, 2-butene, isobutylene, a mixed butene, chloropropene, 2-chloropropene, styrene, o-vinyltoluene, m-vinyltoluene, p-vinyltoluene, o-chlorostyrene, m-chlorostyrene, p-chlorostyrene, styrene dimer, styrene trimer, α-methylstyrene, α-methylstyrene dimer, α-ethylstyrene, α-ethylstyrene dimer, α-propylstyrene, α-propylstyrene dimer, α-isopropylstyrene, α-isopropylstyrene dimer, α-butylstyrene, α-butylstyrene dimer, α-isobutylstyrene, α-isobutylstyrene dimer, α-sec-butylstylene, α-secbutylstyrene dimer, α-tert-butylstyrene, α-tert-butylstyrene dimer, α,4-dimethylstyrene and α,4-dimethylstyrene dimer.

The phenol compound of formula (III-b) includes, for example, p-cresol, p-ethylphenol, p-propylphenol, p-isopropylphenol, p-butylphenol, p-isobutylphenol, p-sec-butylphenol, p-tert-butylphenol, p-(α-methylbenzyl)phenol, p-(α,α-dimethylbenzyl)phenol, p-(α,4-dimethylbenzyl)phenol, p-(α,α,4-trimethylphenyl)phenol, p-(4-chloro-α-methylbenzyl)phenol, p-chlorophenol and p-chloromethylphenol; and the phenol compound of formula (III-c) includes, for example, o-cresol, o-ethylphenol, o-propylphenol, o-isopropylphenol, o-butylphenol, o-isobutylphenol, o-sec-butylphenol, o-tert-butylphenol, o-(methylbenzyl)phenol, o-(α,α-dimethylbenzyl)phenol, o-(α,4dimethylbenzyl)phenol, o-(α,α,4-trimethylphenyl)phenol, o-(4-chloro-α-methylbenzyl)phenol, o-chlorophenol and o-chloromethylphenol.

The 3,6-di-substituted phenol compound of formula (I-b) can be prepared by reacting the olefin compound of formula (II) with a phenol compound of formula (III-d):

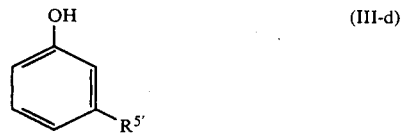

wherein $R^{5'}$ is the same as $R^5$ other than hydrogen.

The olefin compound of formula (II) is the same as defined above.

The phenol compound of formula (III-d) includes, for example, m-cresol, m-ethylphenol, m-propylphenol, m-isopropylphenol, m-butylphenol, m-isobutylphenol, m-sec-butylphenol, m-tert-butylphenol, m-(α-methylbenzyl)phenol, m-(α,α-dimethylbenzyl)phenol, m-(α,4-dimethylbenzyl)phenol, m-(α,α,4-trimethylbenzyl)phenol, m-(4-chloro-α-methylbenzyl)phenol, m-chlorophenol and m-chloromethylphenol.

The catalysts which are the most important characteristic of the present invention, are a phosphorus compound and a carboxylic acid compound.

The phosphorus compounds as one of the catalysts, are inorganic phosphorus compounds and include, for example, phosphoric acid, hypophosphoric acid, pyrophosphoric acid, phosphorous acid, hypophosphorous acid or polyphosphoric acid; phosphorus pentoxide; a phosphorus halide such as phosphorus trichloride, phosphorus pentachloride, phosphorus tribromide, phosphorus pentabromide, phosphorus trifluoride, phosphorus pentafluoride, phosphorus triiodide or phosphorus pentaiodide; a phosphorus oxyhalide such as phosphorus oxychloride, phosphorus oxybromide, phosphorus oxyfluoride or phosphorus oxyiodide; and an ester of phosphoric and phosphorous acids; preferably phosphoric acid, phosphorous acid, hypophosphorous acid or ester of phosphoric acid and phosphorous acid can be used. These phosphorus compounds can be used with or without water.

Further, a carboxylic acid includes, for example, an alkanecarboxylic acid such as formic acid, acetic acid, propionic acid, butyric acid or lactic acid; and a halogenated alkanecarboxylic acid such as chloroacetic acid, dichloroacetic acid, trichloroacetic acid, bromoacetic acid, dibromoacetic acid, tribromoacetic acid, fluoroacetic acid, difluoroacetic acid, trifluoroacetic acid, iodoacetic acid, diiodoacetic acid, triiodoacetic acid, α-chloropropionic acid, α-bromopropionic acid, α-fluoropropionic acid or α-iodopropionic acid; preferably formic acid, acetic acid, propionic acid, chloroacetlc acid, dichloroacetic acid and α-chloropropionic acid can be used. These carboxylic acid compounds can be employed with or without water.

More preferably, the reaction of the present invention can be carried out by a combination of the phosphorus compound which is selected from phosphoric acid, phosphorous acid, hypophosphorous acid and an ester of phosphoric acid or phosphorous acid, and the carboxylic acid compound which is selected from formic acid, acetic acid, propionic acid, chloroacetic acid, dichloroacetic acid or a-chloropropionic acid.

The reaction can be carried out by using an olefin at the above theoretical amount of the objective compound to a phenol compound. The amount of a phosphorus compound and a carboxylic acid compound used as catalysts ranges from 0.5 to 300 mole % and from 1.0 to 400 mole %, respectively, to phenol compounds. It preferably ranges from 5 to 200 mole % for both. Moreover, the rate of amount of the phosphorus compound to the carboxylic acid compound is the range of 10:1–1:10 molar ratio.

The reaction temperature may vary depending on the starting materials and catalysts, and is 0°–200° C., preferably at 70°–150° C.

In the course of the reaction of the invention, the use of a solvent is not always necessary. But, if necessary, a conventional non-aqueous solvent such as hexane, heptane, octane, toluene or xylene can be used.

Moreover, the catalysts can be easily removed by washing with water and recovered from the reaction system, and reutilized.

At the end of the reaction, 2,4- or 3,6-di-substituted phenol compounds obtained by the present invention can be separated and purified by a conventional manner such as distillation, separation and so on.

By using the phosphorus compound and the carboxylic acid compound as catalysts as shown in examples and reference examples, the present invention has the following characteristics:

(1) Only one species of 2,4- or 3,6-di-substituted compounds can be obtained in a high yield and selectively.

(2) The objective phenol compounds can be obtained by one-step reaction without causing the transferation and disproportionation reaction.

(3) The by-products are rarely formed even by using an olefin at the above theoretical amount to a phenol compound and accordingly, the objective phenol compounds can be obtained without controling the amount of the starting materials.

(4) The phosphorus compound and the carboxylic acid compound using as catalysts can be recovered easily and reutilized.

(5) The delicate adjustment of the reaction can be easily made because it is possible to change the potency of the carboxylic acid compound as a catalyst stepwise in the reaction by halogenation, e.g. from acetic acid to chloroacetic acid and further to dichloroacetic acid.

Therefore, the methods of the present invention are enable to make the separation procedures easy, make the reaction process and time short, not to produce any colored resultant product, and reduce that cost in manufacturing procedures.

The 2,4- or 3,6-di-substituted phenol compounds obtained by the present invention are useful as intermediate compounds for the synthesis of loading materials of rubbers, antioxidants, plasticizers, phenol resins or developers of the thermosensitive and pressure-sensitive recording sheets and so on.

For example, 2,2'-methylenebis(6-tert-butyl-4-methylphenol) and 2,2'-thiobis(6-tert-butyl-4-methylphenol) and the like as antioxidants can be derived from 2-tert-butyl-4-methylphenol obtained by Example 3 of the present invention by a conventional synthesis manner.

The present invention will be more concretely explained by the following examples and reference examples, but they should not be thought to limit the scope of the invention.

EXAMPLE 1

A 100 ml-autoclave was charged with 28 g of phenol, 4 g of phosphoric acid and 20 g of acetic acid, and heated at 120° C. Thereto was gradually added 34 g of isobutylene and the mixture was stirred at 120° C. for 3 hours. The reaction mixture consisted of 1.0% of phenol, 14% of 2-tert-butylphenol, 11% of 4-tert-butylphenol and 74% of 2,4-di-tertbutylphenol, when analyzed with gas chromatography as a % area. 2,6-Di-tert-butylphenol and 2,4,6-tri-tert-butylphenol were not formed. Phosphoric acid and acetic acid were removed by washing with water. Distillation at 170° C. gave 44 g of 2,4-di-tert-butylphenol. Each spectra of NMR, MS and IR of the objective compound was identical with those of the standard compound.

EXAMPLE 2

To a mixture of 28 g of phenol, 10 g of phosphoric acid and 10 g of propionic acid as gradually added 45 g of isobutylene, and stirred at 120° C. for 5 hours. The transparent resulting mixture consisted of 10% of 2-tert-butylphenol, 9% of 4-tert-butylphenol and 81% of 2,4-di-tert-butylphenol, and a trace amount of 2,6-di-tert-butylphenol and 2,4,6-tri-tert-butylphenol, when analyzed with gas chromatography. The mixture was distilled in a similar manner as Example 1 to give 47 g of 2,4-di-tert-butylphenol.

EXAMPLE 3

To a mixture of 32 g of p-cresol, 10 g of monochloroacetic acid and 5 g of phosphorous acid as gradually added 20 g of isobutylene, and stirred at 120° C. for 3 hours. The resulting mixture consisted of 98.0% of 2-tert-butyl-4-methylphenol and 2.0% of 2,6-di-tert-butyl-4-methylphenol, when analyzed with gas chromatography. The mixture was distilled in a similar manner as Example 1 to give 45 g of 2-tert-butyl-4-methylphenol.

EXAMPLE 4

To a mixture of 32 g of o-cresol, 15 g of α-chloropropionic acid and 5 g of hypophosphorous acid as gradually added 20 g of isobutylene, and stirred. The resulting mixture consisted of a trace amount of o-cresol, 90% of 4-tert-butyl-2-methylphenol, 3% of 6-tert-butyl-2-methylphenol and 7% of 4,6-di-tert-butyl-2-methylphenol.

EXAMPLE 5

By replacing 32 g of o-cresol with 32 g of m-cresol, the reaction was similarly carried out as Example 4 to give only 6-tert-butyl-3-methylphenol, but not to detect other tert-butylated compounds.

EXAMPLE 6

By replacing 32 g of o-cresol with 32 g of p-ethylphenol, the reaction was similarly carried out as Example 4 to give 2-tert-butyl-4-ethylphenol, and a trace amount of 2,6-di-tert-butyl-4-ethylphenol as another tert-butylated compound.

EXAMPLE 7

By replacing 32 g of o-cresol with 32 g of m-ethylphenol, the reaction was similarly carried out as Example 4 to give only 6-tert-butyl-3-ethylphenol, but not to detect other tert-butylated compounds.

EXAMPLE 8

By replacing 32 g of o-cresol with 32 g of o-ethylphenol, the reaction was similarly carried out as Example 4 to give 96% of 4-tert-butyl-2-ethylphenol, 4% of 6-tert-butyl-2-ethylphenol and a trace amount of 4,6-di-tert-butyl-2-ethylphenol.

EXAMPLE 9

The reaction was similarly carried out as Example 4 except that isobutylene was poured into a mixture of 59.5 g of p-(α-methylbenzyl)phenol, 20 g of phosphoric acid and 20 g of acetic acid to detect only a peak of 2-tert-butyl-4-(α-methylbenzyl)phenol, but not other tert-butylated compounds.

EXAMPLE 10

A four-neck flask with a dropping funnel, a thermometer, a condenser and a stirrer was charged with 5 g of formic acid, 4 g of 85% phosphoric acid and 28 g of phenol, and was heated up to 110° C. Into the reaction mixture was poured 63 g of styrene through a dropping funnel for 3 hours and stirred for an hour. The reaction mixture consisted of 22% of 2-(α-methylbenzyl)phenol, 12% of 4-(α-methylbenzyl)phenol, and 66% of 2,4-di-(α-methylbenzyl)phenol, when analyzed with a gas chromatography as a % area. 2,6-Di-(α-methylbenzyl)phenol and 2,4,6-tri-(α-methylbenzyl)phenol were not formed. Phosphoric acid and acetic acid were removed by washing with water. The organic layer was distilled under reduced pressure at 0.2 mmHg to give 57 g of 2,4-di-(α-methylbenzyl)phenol.

EXAMPLE 11

Except by using 78 g of styrene as olefin, the reaction was similarly carried out as Example 10 to give 14% 2-(α-methylbenzyl)phenol, 8% of 4-(α-methylbenzyl)phenol and 78% of 2,4-di-(α-methylbenzyl)phenol. Further, distillation under reduced pressure gave 67 g of 2,4-di-(α-methylbenzyl)phenol.

EXAMPLE 12

By using 63 g of styrene, 4 g of phosphorous acid and 5 g of propionic acid as olefin, phosphorus compound and carboxylic acid compound, respectively, the reaction was similarly carried out as Example 10 to give 23% of 2-(α-methylbenzyl)phenol, 12% of 4-(α-methylbenzyl)phenol and 65% of 2,4-di-(α-methylbenzyl)phenol, but not to detect other tert-butylated compounds.

EXAMPLE 13

By using 63 g of p-vinyltoluene, 4 g of phosphoric acid and 5 g of formic acid as olefin, phosphorus compound and carboxylic acid compound, respectively, the reaction was similarly carried out as Example 10 to give 21% of 2-(4-methyl-α-methylbenzyl)phenol, 10% of 4-(4-methyl-α-methylbenzyl)phenol and 69% of 2,4-di-(4-methyl-α-methylbenzyl)phenol, but not to detect other tert-butylated compounds.

EXAMPLE 14

By using 78 g of α-methylstyrene, 4 g of phosphoric acid and 5 g of acetic acid as olefin, phosphorus compound and carboxylic acid compound, respectively, the reaction was similarly carried out as Example 10 to give 18% of 2-(α,α-dimethylbenzyl)phenol, 8% of 4-(α,α-dimethylbenzyl)phenol and 74% of 2,4-di-(α,α-dimethylbenzyl)phenol, but not to detect other tert-butylated compounds.

EXAMPLE 15

By using of 63 g of styrene, 4 g of phosphoric acid and 5 g of dichloroacetic acid as olefin, phosphorus compound and carboxylic acid compound, respectively, the reaction was similarly carried out as Example 10 to give 24% of 2-(α-methylbenzyl)phenol, 11% of 4-(α-methylbenzyl)phenol and 65% of 2,4-di-(α-methylbenzyl)phenol, but not to detect other tert-butylated compounds.

EXAMPLE 16

The reaction was similarly carried out as Example 10 except that into a mixture of 32 g of p-cresol, 4 g of hypophosphorous acid and 6 g of α-chloropropionic acid was poured 36 g of styrene to give only 2-(α-methylbenzyl)-4-methylphenol, but not to detect other tert-butylated compounds.

EXAMPLE 17

By replacing 32 g of p-cresol with 32 g of o-cresol, the reaction was similarly carried out as Example 16 to give 90% of 4-(α-methylbenzyl)-2-methylphenol, 2% of 6-(α-methylbenzyl)-2-methylphenol and 8% of 4,6-di-(α-methylbenzyl)-2-methylphenol, but not to detect other tert-butylated compounds.

EXAMPLE 18

By replacing 32 g of p-cresol with 32 g of m-cresol, the reaction was similarly carried out as Example 16 to give only 6-(α-methylbenzyl)-3-methylphenol, but not to detect other tert-butylated compounds.

EXAMPLE 19

By replacing 32 g of p-cresol with 32 g of p-ethylphenol, the reaction was similarly carried out as Example 16 to give only 2-(α-methylbenzyl)-4-ethylphenol, but not to detect other tert-butylated compounds.

EXAMPLE 20

The reaction was similarly carried out as Example 10 except that into a mixture of 59.5 g of p-(α-methylbenzyl)phenol, 25 g of phosphoric acid and 20 g of acetic acid was poured 31 g of styrene to give only 2,4-di-(α-methylbenzyl)phenol, but scarcely to detect other tert-butylated compounds.

REFERENCE EXAMPLE 1

A 100 ml-autoclave was charged with 28 g of phenol and 3 g of methanesulfonic acid, and heated at 120° C. Thereto was gradually added 34 g of isobutylene and the mixture was stirred at 120° C. for 3 hours. The dark red reaction mixture consisted of 2% of phenol, 7% of 2-tert-butylphenol, 9% of 4-tert-butylphenol, 43% of 2,4-di-tert-butylphenol, 8% of 2,6-di-tert-butylphenol and 31% of 2,4,6-tri-tert-butylphenol, when analyzed with a gas chromatography as a % area. The reaction mixture was distilled to give 24 g of 2,4-di-tertbutylphenol.

REFERENCE EXAMPLE 2

The reaction was similarly carried out as Reference example 1 except by replacing methanesulfonic acid with 3 g of phosphoric acid as a catalyst to give 20% of 2-tertbutylphenol, 40% of 4-tert-butylphenol, 32% of 2,4-di-tertbutylphenol, 3% of 2,6-di-tert-butylphenol and 5% of 2,4,6-tri-tert-butylphenol.

REFERENCE EXAMPLE 3

The reaction was similarly carried out as Reference example 1 except by replacing methanesulfonic acid with 3 g of sulfuric acid as a catalyst to give 5% of 2-tert-butylphenol, 24% of 4-tert-butylphenol, 59% of 2,4-di-tert-butylphenol, 2% of 2,6-di-tert-butylphenol and 8% of 2,4,6-tri-tert-butylphenol.

REFERENCE EXAMPLE 4

The reaction was similarly carried out as Reference example 1 except by replacing methanesulfonic acid with 3 g of p-toluenesulfonic acid as a catalyst to give 15% of 2-tert-butylphenol, 16% of 4-tert-butylphenol, 55% of 2,4-di-tert-butylphenol, 2% of 2,6-di-tert-butylphenol and 12% of 2,4,6-tri-tert-butylphenol.

REFERENCE EXAMPLE 5

The reaction was similarly carried out as Reference example 1 except by replacing methanesulfonic acid with 3 g of acetic acid, but the reaction was not completely carried out.

REFERENCE EXAMPLE 6

A four-neck flask with a dropping funnel, a thermometer, a condenser and a stirrer was charged with 3 g of oxalic acid and 28 g of phenol, and was heated up to 110° C. Into the reaction mixture was poured 64 g of styrene through a dropping funnel for an hour and stirred for 3 hours. When analyzed as a % area by using a gas chromatography, the reaction mixture consisted of 40% of 2-(α-methylbenzyl)phenol, 23% of 4-(α-methylbenzyl)phenol, 10% of 2,6-di-(α-methylbenzyl)phenol, 21% of 2,4-di-(α-methylbenzyl)phenol and 4% of 2,4,6-tri-(α-methylbenzyl)phenol.

REFERENCE EXAMPLE 7

The reaction was similarly carried out as Reference example 6 except by using 3 g of methanesulfonic acid as a catalyst to give 8% of 2-(α-methylbenzyl)phenol, 6% of 4-(α-methylbenzyl)phenol, 14% of 2,6-di-(α-methylbenzyl)phenol, 34% of 2,4-di-(α-methylbenzyl)phenol and 38% of 2,4,6-tri-(α-methylbenzyl)phenol.

REFERENCE EXAMPLE 8

The reaction was similarly carried out as Reference example 6 except by using 3 g of phosphoric acid as a catalyst to give 23% of 2-(α-methylbenzyl)phenol, 50% of 4-(α-methylbenzyl)phenol, 5% of 2,6-di-(α-methylbenzyl)phenol and 10% of 2,4-di-(α-methylbenzyl)phenol, but not to detect 2,4,6-tri-(α-methylbenzyl)phenol.

REFERENCE EXAMPLE 9

The reaction was similarly carried out as Reference example 6 by using 3 g of acetic acid as a catalyst, but it was not completely carried out.

REFERENCE EXAMPLE 10

The reaction was similarly carried out as Reference example 6 by using 3 g of dichloroacetic acid as a catalyst, but it was not completely carried out.

What is claimed is:

1. A selective process for preparing a 2,4- or 3,6-disubstituted phenol compound which comprises reacting an olefin compound of the formula:

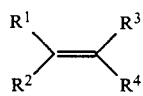

wherein $R^1$ is hydrogen, $C_{1-8}$-alkyl, phenyl or $C_{1-4}$-alkyl substituted-phenyl; and $R_2$, $R_3$ and $R_4$ are the same or different and each is hydrogen or $C_{1-8}$-alkyl; with a phenol compound of the formula:

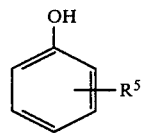

wherein $R^5$ is hydrogen, $C_{1-8}$-alkyl or $-C(R^6)(R^7)CH(R^8)(R^9)$ (wherein $R^6$ is hydrogen, $C_{1-8}$-alkyl, phenyl or $C_{1-4}$-alkyl substituted-phenyl; and $R^7$, $R^8$ and $R^9$ are the same or different and each is hydrogen or $C_{1-8}$-alkyl); in the presence of a phosphorus compound selected from phosphoric acid, hypophosphoric acid, pyrophosphoric acid, phosphorous acid, hypophosphorous acid, polyphosphoric acid, phosphorus pentaoxide, a phosphorus halide, a phosphorus oxyhalide or an ester of phosphoric and phosphorus acid, and a carboxylic acid compound selected from formic acid, acetic acid, propionic acid, chloracetic acid, dichloroacetic acid and α-chloropropionic acid.

2. A selective process for preparing a 2,4-di-substituted phenol compound of the formula:

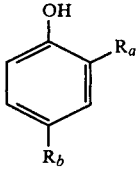

wherein $R_a$ and $R_b$ are the same or different and each is $C_{1-8}$-alkyl or $-C(R^6)(R^7)CH(R^8)(R^9)$ (wherein $R^6$ is hydrogen, $C_{1-8}$-alkyl, phenyl or $C_{1-4}$-alkyl substituted-phenyl; and $R^7$, $R^8$ and $R^9$ are the same or different and each is hydrogen or $C_{1-8}$-alkyl); which comprises reacting an olefin compound of the formula:

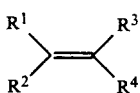

wherein $R^1$ is hydrogen, $C_{1-8}$-alkyl, phenyl or $C_{1-4}$-alkyl substituted-phenyl; and $R^2$, $R^3$ and $R^4$ are the same or different and each is hydrogen or $C_{1-8}$-alkyl; with a phenol compound selected from the group consisting of the compounds of the formulae:

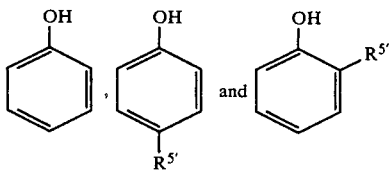

wherein $R^{5'}$, is the same as $R^5$ other than hydrogen; in the presence of a phosphorus compound selected from phosphoric acid, hypophosphoric acid, pyrophosphoric acid, phosphorous acid, hypophosphorous acid, polyphosphoric acid, phosphorus pentaoxide, a phosphorus halide, a phosphorus oxyhalide or an ester of phosphoric and phosphorus acid, and a carboxylic acid compound selected from formic acid, acetic acid, propionic acid, chloroacetic acid, dichloroacetic acid and α-chloropropionic acid.

3. A selective process for preparing a 3,6-di-substituted phenol compound of the formula:

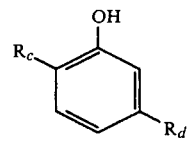

wherein $R_c$ is $C_{1-8}$-alkyl or $-C(R^6)(R^7)CH(R^8)(R^9)$ (wherein $R^6$ is hydrogen, $C_{1-8}$-alkyl, phenyl or $C_{1-4}$-alkyl substituted phenyl; and $R^7$, $R^8$ and $R^9$ are the same or different and each is hydrogen or $C_{1-8}$-alkyl) and $R_d$ is $C_{1-8}$-alkyl or $-C(R^6)(R^7)CH(R^8)(R^9)$ (wherein $R^6$ is hydrogen, $C_{1-8}$-alkyl, phenyl or $C_{1-4}$-alkyl substituted-phenyl; and $R^7$, $R^8$ and $R^9$ are the same or different and each is hydrogen or $C_{1-8}$-alkyl), which comprises reacting an olefin compound of the formula:

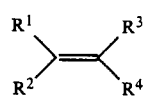

wherein $R^1$ is hydrogen, $C_{1-8}$-alkyl, phenyl or $C_{1-4}$-alkyl substituted-phenyl; and $R^2$, $R^3$ and $R^4$ are the same or different and each is hydrogen or $C_{1-8}$-alkyl; with a phenol compound of the formula:

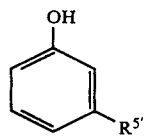

wherein $R^{5'}$, is as defined above; in the presence of a phosphorus compound selected from phosphoric acid, hypophosphoric acid, pyrophosphoric acid, phosphorous acid, hypophosphorous acid, polyphosphoric acid, phosphorus pentaoxide, a phosphorus halide, a phosphorus oxyhalide or an ester of phosphoric and phosphorus acid, and a carboxylic acid compound selected from formic acid, acetic acid, propionic acid, chloroacetic acid, dichloroacetic acid and α-chloropropionic acid.

4. The process of claim 1, 2 or 3 wherein the phosphorus compound is phosphoric acid, phosphorous acid, hypophosphorous acid or an ester of phosphoric and phosphorous acid.

5. The process of claim 1, 2 or 3 wherein the reaction is carried out by a combination of the phosphorus compound which is selected from phosphoric acid, phosphorous acid, hypophosphorous acid and an ester of phosphoric or phosphorous acid, and the carboxylic acid compound which is selected from formic acid, acetic acid, propionic acid, chloroacetic acid, dichloroacetic acid and α-chloropropionic acid.

6. The process of claim 1, 2 or 3, wherein said reaction is carried out by using the phosphorus compound and the carboxylic acid compound in the range of 0.5–300 mole % and the range of 1.0–400 mole % based on the phenol compound.

7. The process of claim 1, 2 or 3, wherein said reaction is carried out at a temperature of from 70° C. to 150° C.

* * * * *